United States Patent
Paradise

(10) Patent No.: US 7,871,647 B1
(45) Date of Patent: *Jan. 18, 2011

(54) TOPICAL TREATMENT OF NEUROPATHY

(75) Inventor: Lou Paradise, Rhineback, NY (US)

(73) Assignee: TPR International, Inc, Rhineback, NY (US)

( * ) Notice: Subject to any disclaimer, the term of this patent is extended or adjusted under 35 U.S.C. 154(b) by 427 days.

This patent is subject to a terminal disclaimer.

(21) Appl. No.: 10/874,122

(22) Filed: Jun. 22, 2004

Related U.S. Application Data

(63) Continuation-in-part of application No. 10/072,410, filed on Feb. 8, 2002, now abandoned.

(51) Int. Cl.
*A61K 36/00* (2006.01)
*A61K 36/28* (2006.01)

(52) U.S. Cl. .................................. 424/725; 424/737

(58) Field of Classification Search .................. None
See application file for complete search history.

(56) References Cited

U.S. PATENT DOCUMENTS 5,788,982 A * 8/1998 Nadoolman et al. ......... 424/440
5,795,573 A * 8/1998 Paradise ..................... 424/737
5,922,332 A * 7/1999 Fossel ....................... 424/401
2003/0003140 A1* 1/2003 Domb et al. ................ 424/449
2003/0083242 A1* 5/2003 Galdes et al. ................ 514/12

OTHER PUBLICATIONS

The Merck Manual; Seventeenth Edition, Lane et al. ed. 1999, pp. 481-482.*
Mayor, S. Trial Shows that Homeopathic Arnica is no Better Than Placebo; British Medical Journal, vol. 326, Iss. 7384 (2003), p. 303.*

* cited by examiner

*Primary Examiner*—Patricia Leith
(74) *Attorney, Agent, or Firm*—John Lezdey and Associates, Inc.

(57) ABSTRACT

A method for treating the pain in the limbs relating to restricted blood flow to nerve endings and reduction in motor and sensory nerve conduction velocities by topically administering a composition containing a plant extract which is a vasodilator, a plant extract which is a stimulator of lymphatic activity and a mobilizer of white blood cells which is derived from snake venom or plants.

3 Claims, No Drawings

TOPICAL TREATMENT OF NEUROPATHY

RELATED APPLICATIONS

This application is a Continuation-in-Part of application Ser. No. 10/072,410 filed Feb. 8, 2002 now abandoned.

FIELD OF THE INVENTION

The present invention relates to the treatment of the symptoms of diseases relating to the restricted blood flow to nerve endings and the limbs of patients. More particularly, there is provided the treatment of the symptoms of such diseases as reflex sympathetic dystrophy syndrome which includes fibromyalgia, toxic neuropathy, and diabetic neuropathy.

BACKGROUND OF THE INVENTION

The article of Hooshmand et al entitled "Complex Regional Pain Syndrome (Reflex Sympathetic Dystrophy Syndrome and Therapy—a Review of 824 Patients" in Pain Digest, Springer—Verlay, New York Inc. 1999 discusses the neuropathic pain with neurovascular dysfunction in patients with complex regional pain syndrome (CRPS) which includes diabetic neuropathy, nutritional neuropathy, fibromyalgia, and the like which involves restriction of blood flow and the reduction of nerve condition velocities.

Fibromyalgia is a disease characterized by pain in the lower extremities and in some cases an autoimmune disease wherein blood circulation is restricted and the nerve endings are affected.

Diabetic neuropathy occupies an important place as one of three major complications of diabetes along with retinopathy and nephropathy.

Diabetic neuropathy is currently categorized into three groups comprising mononeuropathy, symmetrical peripheral polyneuropathy and autonomic neuropathy (Williams Text Book of Endocrinology, 8th Edition, p 1301, Harrison's Principles of Internal Medicine, 12th edition, p 1754).

Mononeuropathy is a focal or multifocal mononeural disorder which appears as lesions of the cerebral nerve or affects soma and/or extremities. Its major symptom emerges as dyskinesia in many cases. It is known to develop more often in elder patients.

Symmetrical peripheral polyneuropathy is the most frequent form of diabetic neuropathy. It generally makes slow progress, so that its patients tend to become aware of the symptoms only after it has reached an advanced stage. The initial symptoms are often a reduced Achilles reflex parasthesis and a decline or absence of vibratory sensibility. Urtication represented as a smarting feeling and then numbness on both feet follow.

With autonomic neuropathy, patients show representative symptoms for autonomic disorder, such as orthostatic hypotension, cardiac rate alteration, dyshidrosis, atony of esophagus or gastric atony, diabetic diarrhea, impotence and others.

As mechanisms for development of these symptoms, metabolic hypothesis and vascular/ischemic hypothesis have been implied. For the former hypothesis, hypergasia of polyol metabolic pathway, a pathway where sorbitol and fructose are produced from glucose provided due to hyperglycemia is considered to be a major contributing factor. Another theory involving a reduced content of myoinositol is related to peripheral nerve disorder. In the latter hypothesis, neuromicrovascular occlusion and/or destruction of blood-nerve barrier are thought to be related to the nerve disorders.

As methods of treatment of diabetic neuropathy, it has been reported that some trial treatments have been conducted during the 1970s and 1980s based upon the hypothesis that abnormality of metabolic factors is viewed as a cause, Greene D A, DeJesus P V Jr., et al. (Effects of insulin and dietary myoinositol on impaired peripheral motor nerve conduction velocity in acute streptozatocin diabetes, J. Clin. Invest., 1975, 55, 6, 1326-36) and Yagihashi S., Nishihira M., et al (Morphometric analysis of the peripheral nerve lesions in experimental diabetes rats, Tohoku J. Exp. Med., 129, 2, 139-49, 1979). These confirmed that peripheral nerve fibers of model rats for diabetic neuropathy were morphologically impaired and NCV was reduced. In addition to that, they reported that when insulin was administered to the rats, improvements in NCV could be observed, thus finding that control over blood glucose level led to improvements in NCV.

Accordingly, current methods of treatment for diabetic neuropathy, dietary therapy and administration of insulin, both mainly proposing to control blood glucose level, administration of aldose reductase inhibitors and aminoguadanine, both mainly proposing to improve abnormal glucose metabolism, administration of troglitazone, and administration of agents for limb ischemia mainly proposing to improve blood flow, have been conducted.

In any treatments, improvement of nerve conduction velocity was not always sufficient when a single drug was used, and methods of treatment by combined use of different therapeutic agents which have different functions have yet to be established. Accordingly, combined drug therapies for diabetic neuropathy aiming at recovering once reduced nerve conduction velocity, have not yet been confirmed.

Toxic neuropathy is similar in symptoms as diabetic neuropathy in that nerve fibers are affected and there is a resultant leg numbness or pricking in the feet.

U.S. Pat. No. 5,981,594 to Okanoto et al discloses the use of a prostaglandin I derivative together with an anti-diabetic agent to hypofunction motor and sensory nerves. However, such treatment has side effects because the prostaglandins are not localized at the sites of the pain.

Because diabetes is a systematic disease affecting many parts of the body, ideal case management requires a team approach. This is especially true for the legs, feet and digits of the feet.

U.S. Pat. No. 5,795,573 to Paradise discloses homeopathic topical pain relieving compositions for relieving pain due to injury or stress utilizing the combination of *Arnica Montana*, *Rhus toxicodendron* and *Aesculus hippocastanum*

The article of Nicole Cryer entitled "Venom & Miracle Medicine?" in Science World, Nov. 1, 1997, p. 1 and 2 discloses the utility of venom-based drugs.

The Edward Dennis Group of the University of California has characterized the enzyme Phospholipase A2 from cobra venom as being involved in eicosanoid productions and phospholipids remodeling in cells involved with inflammation, parturition and neural function.

SUMMARY OF THE INVENTION

According to the invention there is provided a method of treating the symptoms of diseases related to restricted blood flow and nerve impairment wherein there is a reduction in motor and sensory nerve conduction velocities by the topical application of a composition containing vasodilators, stimulants of the lymphatic systems and mobilizers of white blood cell activity. The treatment is particularly useful for patients suffering from CRPS, especially fibromyalgia, diabetic neuropathy, and toxic neuropathy.

More particularly, there is a method for treating a patient having pain caused by a restricted flow of blood and a reduction in motor and sensory nerve conduction velocities in the limbs which comprises topically administering to the site of pain an effective amount to reduce said pain of a composition comprising:

A. about 0.5 to 5% by weight of an extract derived from a plant which is a vasodilator;

B. about 0.5 to 5% by weight of a plant extract which is a stimulator of lymphatic activity;

C. about 0.5 to 5% by weight of a mobilizer of white blood cell activity selected from the group consisting of snake venom and Red Chinese Ginseng, Siberian Ginseng, Korean Ginseng, Goldenseal, Chamomile, and Barberry.

The compositions of the invention include homeopathic preparations and combinations of homeopathic medicines and herbal and/or nutritional supplements.

It is advantageous to include in the compositions components which can heal the skin in those areas which have been damaged as a result of the lack of blood circulation to capillaries and blood vessels.

It is preferable that the compositions contain an effective amount of *Arnica Montana* to improve blood flow, *Lachesis* and *Crotalus horridus* venom to thin the blood and increase enzyme activity, and *Echinacea* to stimulate the lymphatic system to reduce inflammation.

It is a general object of the invention to provide a method for treating the pain of patients suffering from restricted blood circulation and the reduction of nerve conduction velocities.

It is a further object of the invention to treat a patient suffering from CRPS.

It is another object of the invention to improve blood flow and the delivery of vital oxygen and nutrients to nerve cells and surrounding tissues of patients suffering from a disease which restricts blood flow to those areas which are inflamed.

These and other objects and advantages will become more apparent from a reading of the preferred embodiments of the invention.

It is understood that the term "plant" refers to flowers, herbs, vegetable extracts, and tree-bark extracts and the like. Also, the references to snakes refers to snake venom or extracts therefrom and snake venom also means extracts thereof.

PREFERRED EMBODIMENTS OF THE INVENTION

According to the present invention there is provided a method of topically treating a patient suffering from a disease which causes restricted blood flow and nerve impairment, especially to the extremities. The topically applied composition can be in the form of a lotion, cream, gel or salve. It has been found that a synergistic therapeutically effective amount of the combination of a vasodilator, a stimulator of lymphatic activity and a mobilizer of white blood cell activity that can be topically applied at the site of pain and numbness is effective to provide relief from the symptom of the disease causing the problems. That is, for use in connection with CRPS diseases such as fibromyalgia, diabetic neuropathy, toxic neuropathy and the like.

More specifically, the components of the composition comprise the following:

A. Vasodilator—*Arnica Montana*, primrose oil, rosemary, ginger, *Hamamelis*, horse chestnuts, Yohimbe, niacin L-ornithate, and the like.

B. Stimulator of lymphatic activity—*Echinacea Augustofolia*, St. Johns Wort, Belladonna, Devils Claw, Yellow Dock, Burdock, North American Ginseng, Wild Indigo, Pleurisy Root, and Pokeweed.

C. Mobilizers of white blood cell activity—*Lachesis Ninta* venom, *Crotalus horridus* venom, Naja venom, Red Chinese Ginseng, Siberian Ginseng and Korean Ginseng, Goldenseal, Chamomile, and Barberry.

Each of the components can be used in the amount of about 0.5 to 5%, preferably, 0.5 to 2.0% by weight.

Snake venom and venom extracts have been found to have anti-inflammatory activity.

Prostaglandins have been found to improve nerve conduction velocity. However, it should be formed to be advantageous to induce prostaglandin production at the site affected by the disease rather than infusing the entire body. Consequently, the inclusion of 0.5 to 5% by weight of the composition such as primrose oil, flax oil, and crocetin have been found to be beneficial.

The addition of L-arginine and arginine containing peptides have been found to not only produce nitrous oxide at the site to increase blood circulation but also to attract hormones which can help the healing process. Additionally, L-arginine acts as a carrier for obtaining deeper penetration of some of the active ingredients when used in an amount of 0.5 to 5% by weight and can be generally used to produce the nitrous oxide.

Capsaicin has been recognized as aiding blood circulation and masking or relieving pain. Capsaisin can be used especially to relieve pain.

Since cracking and dryness of the feet are some of the symptoms of the diseases involved, namely, anhidrosis, it has been found to be advantageous to include skin conditioning components such as graphite and trace minerals.

Because the body chemistry of individuals is different and the diseases may be in different phases it is preferable in some cases to use a variety of different components which can produce the desired effect on contact to produce a synergism.

The amounts of the different constituents of the compositions according to the invention are those traditionally used in the pharmaceutical field.

When the composition of the invention is an emulsion, the proportion of the fatty phase can range from 5% to 80% by weight and preferably from 5% to 50% by weight, relative to the total weight of the composition. The oils, emulsifiers and coemulsifiers used in the composition in emulsion form are chosen from those traditionally used in the cosmetics. The emulsifier and the coemulsifier are present in the composition in a proportion ranging from 0.3% to 30% by weight, and preferably 0.5 to 30% or, better still from 0.5 to 20%, by weight, relative to the total weight of the composition. The emulsion can, in addition, contain lipid vesicles.

When the compositions of the invention is an oily gel or solution, the fatty phase can represent more than 90% of the total weight of the composition.

In a known manner, the composition of the invention may also contain adjuvants which are customary in the pharmaceutical field, such as hydrophilic or lipophilic gelling agents, hydrophilic or lipophilic active agents, preservatives, antioxidants, solvents, perfumes, fillers. The amounts of these different adjuvants are those traditionally used in the pharmaceutical or dermatological field, and are, for example, from 0.01% to 10% of the total weight of the composition. Those adjuvants, depending on their nature, may be introduced into the fatty phase, into the aqueous phase and/or lipid spherules.

As oils which can be used in the invention, are those which do not clog or block pores such as vegetable oils, liquid fraction of sheat butter, sunflower oil and animal oils (perhydrosquantene) may be mentioned. Mineral oil lanolin and petroleum oils block pores so as to prevent the skin from releasing toxins.

Fatty alcohols and fatty acids (stearic acid) may also be used as fatty substances.

As emulsifiers which can be used in the invention, glycerol stearate, polysorbate 60 and the PEG-6/PEG-32/glycol stearate mixture sold under the name of Tefose® 63 by the company Gattefosse may be mentioned as examples.

As hydrophilic gelling agents, carboxyvinyl polymers (carbomer), acrylic copolymers such as acrylate/alkylacylate copolymers, polyacrylamides, polysaccarides such as hydroxypropylcellulose, clays and natural gums may be mentioned.

Lipophilic gelling agents, clays such as bentones, metal salts of fatty acids such as aluminum stearates and hydrophobic silica, or alternatively ethylcellulose and polyethylene may be mentioned.

Natural gums which may be used includes xantham gum, alginates and the like. As hydrophilic active agents, proteins or protein hydrolysates, amino acids, polyols, urea, allantonin, sugars and sugar derivatives, water-soluble vitamins, starch and plant extracts, in particular those of the Aloe vera may be used.

As lipophilic active, agents, retinol (vitamin A) and its derivatives, tocopherol (vitamin E) and its derivatives, essential fatty acids, ceramides and essential oils may be used. These agents add extra moisturizing or skin softening features when utilized.

The compositions of the invention may include other plant or herbal extracts which reduce irritation. For example, there may be utilized extracts of Paraguay tea, Kola and Guarana, which provide a source of methylxanthines, saponius, tannins, and glycosides that have been shown to be anti-inflammatory and can be used to treat irritations and cracked skin.

Suitable herbs which can be used also to help healing of the skin include *symphytum, officianalis, Moschus moscheferous*, Cow bezoar, *Pripalia geniculata, Plantago asiatica, Causticum, Helianthemum canadense, Ornithogalum umbellatum, Clematis crispa, Impatiens pallida, Pruaus Cerasus*, and the like.

A surfactant can be included in the composition so as to provide deeper penetration of the ingredients. Although natural surfactants are preferred others such as isopropyl myristate can be used.

Other ingredients may be used, preferably, in amounts from about 0.5% to 2% by weight.

The following examples illustrating the compositions of the invention are not intended to limit the scope of the invention. The amounts indicated are by weight percent unless otherwise noted.

Example 1

A homeopathic gel prepared by admixing the following ingredients.

| Ingredient | Wt. % |
| --- | --- |
| Carbomer 940 | 2.10 |
| Xantham Gum | 0.15 |
| Propylene glycol | 51.94 |

-continued

| Ingredient | Wt. % |
| --- | --- |
| Dipropylene glycol | 10.00 |
| Ethoxydiglycol | 15.00 |
| Dimethylisosorbide | 10.00 |
| Aloe Vera gel | 2.00 |
| Surfactant | 0.05 |
| *Arnica Montana* | 2.50 |
| *Echinacea augustofolia* extract | 2.50 |
| *Lachenis Malta* venom | 2.00 |
| *Crotalus horridus* venom | 1.76 |
| | 100.00% |

Although the specific activity of each of either plants or herbs have been recognized, it has been surprisingly found that the combination as now claimed has been found to produce the desired effect. The composition is applied to the limb having pain 1-8 times per day.

Example 2

A crème was formed by admixing the following ingredients.

| Ingredient | Wt. % |
| --- | --- |
| *Aesculus hippocastanum* extract | 6 mcg/g |
| *Arnica Montana* extract | 6 mcg/g |
| L-arginine | 6 mcg/g |
| *Echinacea augustfolia* extract | 6 mcg/g |
| *Rhus toxicondendron* extract | 6 mcglg |
| *Ruta graveoleus* extract | 6 mcg/g |
| Graphites | 6 mcg/g |
| *Crotalus horridus* extract | 0.08 mcg/g |
| *Heloderma horridum* extract | 0.08 mcg/g |
| *Lachesis* extract | 0.08 mcg/g |
| *Naja* extract | 0.08 mcg/g |
| Isopropyl myristate | 30 mg/g |
| Brij 72 | 2 mg/g |
| Brij 72IS | 2 mg/g |
| Water | 83 mg/g |
| Methyl paraben | 0.2 mg/g |
| Propyl paraben | 20 mcg/g |
| Glycerine | 3 mg/g |
| 20% NaOH | 3 mg/g |
| Dowcil 200 | 50 mcg/g |
| Akodel 112 | 2 mg/g |

The crème may be used to treat cracked skin on feet or anhidrosis which is associated with CRPS.

Example 3

A lotion is prepared by admixing the following ingredients:

| Ingredient | Wt. % |
| --- | --- |
| Ginger | 1.10 |
| Propylene Glycol Stearate | 6.50 |
| Isocetyl alcohol | 5.00 |
| PEG-100 Stearate | 1.20 |
| Water | 69.90 |
| *Echinacea augustfolia* extract | 3.00 |
| Methyl paraben | 0.20 |
| Propylene glycol | 12.00 |

-continued

| Ingredient | Wt. % |
|---|---|
| Sorbitan palmitate | 0.60 |
| *Arnica Montana* | 3.00 |
| *Aesculus hippocastanum* extract | 2.00 |
| Barberry | 1.00 |
| Mate extract | 0.50 |
| | 100% |

If desired, 3% by weight capsaicin can be added. The lotion can be used to treat a patient suffering from fibromyalgia.

Example 4

Preparation of a Gel

| Ingredients | % W/W |
|---|---|
| *Arnica Montana* | 5.0 |
| Primrose oil | 3.0 |
| Arginine base (10% solution) (Ajinomoto) | 5.0 |
| Carbopol 940 | 0.4 |
| Butylene glycol | 6.5 |
| *Echinacea augustfolia* | 3.0 |
| Chamomile glycolic extract | 3.0 |
| *Crotalus horridus* venom | 0.5 |
| Preservative | 0.1 |
| Fragrance | 0.1 |
| Deionized water | q.s. |
| | 100% |

To 20 ml of water with stirring is added the Carbopol 940. The mixture is stirred until hydration is complete and then butylene glycol is added. The arginine base is then added to the mixture. The remaining ingredients are mixed together and added to the first mixture. The mixing is continued until uniform. The composition can be applied 1-8 times daily to reduce the pain resulting from CRPS.

Example 5

A gel is prepared by admixing the following ingredients.

| Ingredient | Wt. % |
|---|---|
| 1. Propylene Glycol | 43.00 |
| 2. Polyacrylic acid | 2.10 |
| 3. Dipropylene Glycol | 16.00 |
| 4. Xantham Gum | 0.15 |
| 5. Ethoxydiglycol | 15.00 |
| 6. Dimethylisosorbide | 10.00 |

-continued

| Ingredient | Wt. % |
|---|---|
| 7. Ascorbic Acid | 2.00 |
| 8. Chloroxylenol | 0.20 |
| 9. Linoleamidopropyl PG-diammonium chloride phosphate | 1.50 |
| 10. Glycereth 4.5 Lactate | 2.00 |
| 11. *Naja* venom extract | 2.00 |
| 12. *Echinacea augustfolia* | 2.00 |
| 13. Octoxynol-9 | 0.50 |
| 14. Primrose Oil | 2.00 |
| 15. Cocamidopropyl PG-dimon chloride phosphate | 1.00 |
| 16. Water | 6.00 |
| 17. Ginger | 0.44 |

Ingredients 1 and 2 are mixed to disperse and form a gel. About 80% of ingredient 3 is mixed with ingredient 4, added to the gel slightly heated with admixture. The balance of 3 is mixed with ingredients 5-17 and added to the gel at 38 degrees C. After mixing, the pH is adjusted to about 4 and then the gel is brought to room temperature.

*Arnica Montana* may also be added to have a plurality of dual acting ingredients. Capsiacin together with the ginger can be used to relieve pain.

The invention claimed is:

1. A composition for treating fibromyalgia pain consisting essentially of the following ingredients:

| Ingredient | Concentration |
|---|---|
| *Aesculus hippocastanum* extract | 6 mcg/g |
| *Arnica montana* extract | 6 mcg/g |
| L-arginine | 6 mcg/g |
| *Echinacea augustfolia* extract | 6 mcg/g |
| *Rhus toxicondendron* extract | 6 mcg/g |
| *Ruta graveoleus* extract | 6 mcg/g |
| graphites | 6 mcg/g |
| *Crotalus horridus* extract | 0.08 mcg/g |
| *Heloderma horridum* extract | 0.08 mcg/g |
| *Lachesis* extract | 0.08 mcg/g |
| *Naja* extract | 0.08 mcg/g |
| isopropyl myristate | 30 mg/g |
| water | 83 mg/g |
| methyl paraben | 0.2 mg/g |
| propyl paraben | 20 mcg/g |
| glycerine | 3 mg/g |
| 20% NaOH | 3 mg/g, |
| and capsaicin. | |

2. The composition of claim 1 wherein said composition is a gel, cream, emulsion, salve or lotion.

3. A method for treating a patient suffering from pain caused by fibromyalgia, comprising topically applying an effective amount of the composition of claim 1 or claim 2 to the site of said pain in a patient in need thereof.

* * * * *